(12) United States Patent
Kim et al.

(10) Patent No.: US 12,222,646 B2
(45) Date of Patent: Feb. 11, 2025

(54) POLYPEPTIDE, PHOTORESIST COMPOSITION INCLUDING THE SAME, AND METHOD OF FORMING PATTERN USING THE SAME

(71) Applicant: Samsung Electronics Co., Ltd., Suwon-si (KR)

(72) Inventors: Jinha Kim, Hwaseong-si (KR); Soonchun Chung, Seoul (KR); Jieun Kim, Suwon-si (KR); Joonsong Park, Suwon-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 0 days.

(21) Appl. No.: 17/741,692

(22) Filed: May 11, 2022

(65) Prior Publication Data
US 2023/0176480 A1    Jun. 8, 2023

(30) Foreign Application Priority Data
Dec. 2, 2021  (KR) .................. 10-2021-0171197

(51) Int. Cl.
| G03F 7/038 | (2006.01) |
| C07K 14/00 | (2006.01) |
| G03F 7/20 | (2006.01) |
| G03F 7/32 | (2006.01) |

(52) U.S. Cl.
CPC .......... G03F 7/0387 (2013.01); C07K 14/001 (2013.01); G03F 7/32 (2013.01); G03F 7/2006 (2013.01)

(58) Field of Classification Search
CPC ........ G03F 7/0387; G03F 7/32; G03F 7/2006; C07K 14/001
See application file for complete search history.

(56) References Cited

U.S. PATENT DOCUMENTS

| 5,989,894 A | 11/1999 | Lewis et al. |
| 2003/0091927 A1 | 5/2003 | Lee et al. |
| 2005/0090641 A1 | 4/2005 | Valluzzi et al. |
| 2006/0090641 A1 | 5/2006 | Noda |
| 2008/0160446 A1 | 7/2008 | Meagley |
| 2011/0023154 A1 | 1/2011 | Bedell et al. |
| 2014/0011739 A1* | 1/2014 | Klatzmann ............... A61P 3/10 514/11.7 |
| 2022/0372078 A1 | 11/2022 | Chung et al. |

FOREIGN PATENT DOCUMENTS

| CN | 108084268 A | * | 5/2018 | |
| EP | 294979 A1 | | 12/1988 | |
| JP | 2005263631 A | | 9/2005 | |
| JP | 6098771 A | | 6/2017 | |
| KR | 20160017295 A | | 2/2016 | |
| KR | 20220157526 A | | 11/2022 | |
| WO | WO-0181581 A2 | * | 11/2001 | .......... C07K 14/195 |
| WO | 2003-008540 A2 | | 1/2003 | |
| WO | 2015-060159 A1 | | 4/2015 | |
| WO | 2017-138002 A1 | | 8/2017 | |

OTHER PUBLICATIONS

Machine translation of WO 2015060159 A1, pp. 1-29, accessed Aug. 11, 2023.*
Seq ID No. 12 in WO 2015060159 A1, pp. 1-22.*
Uclacyanin 1-like [Oryza glaberrima], from https://www.ncbi.nlm.nih.gov/protein/2348221665, Nov. 25, 2022, pp. 1-2.*
Glucagon, from PubChem, pp. 1-4, accessed Aug. 15, 2023.*
Toda et al, 50. The Complete Amino Acid Sequence of Taka-amylase A, Proc. Japan Acad., 1982, 58, pp. 208-212.*
Machine translation of JP 2005263631 A, pp. 1-20, accessed Aug. 11, 2023.*
Seq ID No. 85 in JP 2005263631 A, pp. 1-3.*
Bacteriocin carnobacteriocin B2, from https://www.ncbi.nlm.nih.gov/protein/P38580.1?report=genbank&log$=protalign&blast_rank=1&RID=S3W7TGS8016, 2023, pp. 1-2.*
Machine translation of CN108084268A, pp. 1-12. accessed Dec. 19, 2023.*
Seq ID No. 28916 in WO 0181581 A2, p. 1, accessed Dec. 19, 2023.*
Seq ID No. 135 in US 20140011739 A1, pp. 1-2, accessed Dec. 19, 2023.*
Benjamin B. Minkoff, et al., Covalent Modification of Amino Acids and Peptides Induced by IonizingRadiation from an Electron Beam Linear Accelerator Used in Radiotherapy, Radiation Research 191, 447-459 (2019).
English Abstract of JP 2005-263631.
English Abstract of KR 2016-0017295.
English Abstract of WO 2015-060159.
Extended European Search Report issued in EP Patent Application No. 22173975.8, dated Dec. 20, 2022.
Jonathan A. Kluge, et al., Optimizing Molecular Weight of Lyophilized Silk As a Shelf-Stable Source Material, ACS Biomater. Sci. Eng. 2016, 2, 595-605.
Joonhan Park, et al., Eco-friendly photolithography using water-developable pure silk fibroin, RSC Adv., 2016, 6, 39330-39334.
Sunghwan Kim, et al., All-water-based electron-beam lithography using silk as a resist, Nature Nanotechnology, vol. 9, Apr. 2014, 5 pp., www.nature.com/naturenanotechnology.

* cited by examiner

*Primary Examiner* — Li N Komatsu
(74) *Attorney, Agent, or Firm* — CANTOR COLBURN LLP (57) ABSTRACT

A polypeptide, a photoresist composition including the polypeptide, and a method of forming patterns by using the photoresist composition.

6 Claims, 2 Drawing Sheets

Specification includes a Sequence Listing.

SEQUENCE LISTING

```
<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: Artificial polypeptide
<220> FEATURE:
<221> NAME/KEY: FirstRepeatUnit1
<222> LOCATION: (1)..(6)

<400> SEQUENCE: 1

Gly Ala Gly Ala Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Artificial polypeptide
<220> FEATURE:
<221> NAME/KEY: FirstRepeatUnit2
<222> LOCATION: (1)..(4)

<400> SEQUENCE: 2

Gly Ala Ala Ser
1

<210> SEQ ID NO 3
<211> LENGTH: 4
<212> TYPE: PRT
<213> ORGANISM: Artificial Sequence
<220> FEATURE:
<223> OTHER INFORMATION: Artificial polypeptide
<220> FEATURE:
<221> NAME/KEY: SecondRepeatUnit1
<222> LOCATION: (1)..(4)

<400> SEQUENCE: 3

Gly Ala Ser Tyr
1

<210> SEQ ID NO 4
<211> LENGTH: 6
<212> TYPE: PRT
<213> ORGANISM: Artificial Sequence
<220> FEATURE:
<223> OTHER INFORMATION: Artificial polypeptide
<220> FEATURE:
```

```
<221> NAME/KEY: SecondRepeatUnit2
<222> LOCATION: (1)..(6)

<400> SEQUENCE: 4

Gly Ala Gly Ala Ser Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Artificial polypeptide
<220> FEATURE:
<221> NAME/KEY: SecondRepeatUnit3
<222> LOCATION: (1)..(8)

<400> SEQUENCE: 5

Gly Ala Gly Val Gly Ala Ser Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Artificial polypeptide
<220> FEATURE:
<221> NAME/KEY: SecondRepeatUnit4
<222> LOCATION: (1)..(8)

<400> SEQUENCE: 6

Gly Ala Gly Ala Gly Ala Ser Tyr
1               5

<210> SEQ ID NO 7
<211> LENGTH: 10
<212> TYPE: PRT
<213> ORGANISM: Artificial Sequence
<220> FEATURE:
<223> OTHER INFORMATION: Artificial polypeptide
<220> FEATURE:
<221> NAME/KEY: RegionH1
<222> LOCATION: (1)..(10)

<400> SEQUENCE: 7

Gly Ala Gly Ala Gly Ser Gly Ala Ala Ser
1               5                   10

<210> SEQ ID NO 8
<211> LENGTH: 4
<212> TYPE: PRT
<213> ORGANISM: Artificial Sequence
<220> FEATURE:
<223> OTHER INFORMATION: Artificial polypeptide
<220> FEATURE:
<221> NAME/KEY: RegionH2
<222> LOCATION: (1)..(4)

<400> SEQUENCE: 8

Gly Ala Ala Ser
1

<210> SEQ ID NO 9
<211> LENGTH: 42
<212> TYPE: PRT
<213> ORGANISM: Artificial Sequence
<220> FEATURE:
<223> OTHER INFORMATION: Artificial polypeptide
```

```
<220> FEATURE:
<221> NAME/KEY: SynthesisExample1
<222> LOCATION: (1)..(42)
<223> OTHER INFORMATION: HA1B4

<400> SEQUENCE: 9

Gly Ala Gly Ala Gly Ser Gly Ala Ala Ser Gly Ala Gly Ala Gly Ser
1               5                   10                  15

Gly Ala Gly Ala Gly Tyr Gly Ala Gly Val Gly Ala Gly Tyr Gly Ala
            20                  25                  30

Gly Tyr Gly Ala Gly Ala Gly Ala Gly Tyr
        35                  40

<210> SEQ ID NO 10
<211> LENGTH: 42
<212> TYPE: PRT
<213> ORGANISM: Artificial Sequence
<220> FEATURE:
<223> OTHER INFORMATION: Artificial polypeptide
<220> FEATURE:
<221> NAME/KEY: SynthesisExample2
<222> LOCATION: (1)..(42)
<223> OTHER INFORMATION: 14-A

<400> SEQUENCE: 10

Gly Ala Gly Ala Gly Ser Gly Ala Ala Ser Gly Ala Gly Ala Gly Ser
1               5                   10                  15

Gly Ala Gly Ala Ala Tyr Gly Ala Gly Val Gly Ala Ala Tyr Gly Ala
            20                  25                  30

Ala Tyr Gly Ala Gly Ala Gly Ala Ala Tyr
        35                  40

<210> SEQ ID NO 11
<211> LENGTH: 42
<212> TYPE: PRT
<213> ORGANISM: Artificial Sequence
<220> FEATURE:
<223> OTHER INFORMATION: Artificial polypeptide
<220> FEATURE:
<221> NAME/KEY: SynthesisExample3
<222> LOCATION: (1)..(42)
<223> OTHER INFORMATION: 14-P

<400> SEQUENCE: 11

Gly Ala Gly Ala Gly Ser Gly Ala Ala Ser Gly Ala Gly Ala Gly Ser
1               5                   10                  15

Gly Ala Gly Ala Pro Tyr Gly Ala Gly Val Gly Ala Pro Tyr Gly Ala
            20                  25                  30

Pro Tyr Gly Ala Gly Ala Gly Ala Pro Tyr
        35                  40

<210> SEQ ID NO 12
<211> LENGTH: 42
<212> TYPE: PRT
<213> ORGANISM: Artificial Sequence
<220> FEATURE:
<223> OTHER INFORMATION: Artificial polypeptide
<220> FEATURE:
<221> NAME/KEY: SynthesisExample4
<222> LOCATION: (1)..(42)
<223> OTHER INFORMATION: 14-S

<400> SEQUENCE: 12

Gly Ala Gly Ala Gly Ser Gly Ala Ala Ser Gly Ala Gly Ala Gly Ser
1               5                   10                  15
```

Gly Ala Gly Ala Ser Tyr Gly Ala Gly Val Gly Ala Ser Gly Ala
                20                  25                  30

Ser Tyr Gly Ala Gly Ala Gly Ala Ser Tyr
        35                  40

<210> SEQ ID NO 13
<211> LENGTH: 42
<212> TYPE: PRT
<213> ORGANISM: Artificial Sequence
<220> FEATURE:
<223> OTHER INFORMATION: Artificial polypeptide
<220> FEATURE:
<221> NAME/KEY: SynthesisExample5
<222> LOCATION: (1)..(42)
<223> OTHER INFORMATION: 14-D

<400> SEQUENCE: 13

Gly Ala Gly Ala Gly Ser Gly Ala Ala Ser Gly Ala Gly Ala Gly Ser
1               5                   10                  15

Gly Ala Gly Ala Asp Tyr Gly Ala Gly Val Gly Ala Asp Tyr Gly Ala
                20                  25                  30

Asp Tyr Gly Ala Gly Ala Gly Ala Asp Tyr
        35                  40

<210> SEQ ID NO 14
<211> LENGTH: 42
<212> TYPE: PRT
<213> ORGANISM: Artificial Sequence
<220> FEATURE:
<223> OTHER INFORMATION: Artificial polypeptide
<220> FEATURE:
<221> NAME/KEY: SynthesisExample6
<222> LOCATION: (1)..(42)
<223> OTHER INFORMATION: 14-K

<400> SEQUENCE: 14

Gly Ala Gly Ala Gly Ser Gly Ala Ala Ser Gly Ala Gly Ala Gly Ser
1               5                   10                  15

Gly Ala Gly Ala Lys Tyr Gly Ala Gly Val Gly Ala Lys Tyr Gly Ala
                20                  25                  30

Lys Tyr Gly Ala Gly Ala Gly Ala Lys Tyr
        35                  40

<210> SEQ ID NO 15
<211> LENGTH: 9
<212> TYPE: PRT
<213> ORGANISM: Artificial sequence
<220> FEATURE:
<223> OTHER INFORMATION: Artifical polypeptide
<220> FEATURE:
<221> NAME/KEY: MISC_FEATURE
<222> LOCATION: (1)..(1)
<223> OTHER INFORMATION: Xaa is Gly or Ala
<220> FEATURE:
<221> NAME/KEY: MISC_FEATURE
<222> LOCATION: (2)..(5)
<223> OTHER INFORMATION: (Ala-Xaa)n where n is 2 is shown. n can also be
      1.
<220> FEATURE:
<221> NAME/KEY: MISC_FEATURE
<222> LOCATION: (3)..(3)
<223> OTHER INFORMATION: Xaa is Gly or Ala
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)

```
<223> OTHER INFORMATION: Xaa is Ser or Ala

<400> SEQUENCE: 15

Xaa Ala Xaa Ala Xaa Xaa Ala Ala Ser
1               5
```

POLYPEPTIDE, PHOTORESIST COMPOSITION INCLUDING THE SAME, AND METHOD OF FORMING PATTERN USING THE SAME

CROSS-REFERENCE TO RELATED APPLICATION

This application claims priority under 35 U.S.C. § 119 to Korean Patent Application No. 10-2021-0171197, filed on Dec. 2, 2021, in the Korean Intellectual Property Office, and all the benefits accruing therefrom, the disclosure of which in its entirety is herein incorporated by reference.

BACKGROUND

1. Field

The present disclosure relates to a polypeptide, a photoresist composition including the polypeptide, and a method of forming patterns by using the photoresist composition.

2. Description of the Related Art

The high-integration of semiconductor devices has contributed to a growing need for finer (e.g., higher) resolution and more precise patterning in the devices. Chemically amplified materials are routinely used for photoresists; however, such materials can result in acid diffusion during photoresist development, which in turn, makes it more difficult to achieve fine or high-resolution patterns in a semiconductor device. Moreover, many of the present materials used to form and/or develop the photoresist films may be potentially hazardous to human health and the environment.

Accordingly, there is a demand for eco-friendly photoresist materials that are suitable for achieving fine or high-resolution patterns, e.g., in semiconductor devices, and reduce or eliminate the need for potentially hazardous chemicals in the patterning process or the release of such chemicals/materials into the environment.

SUMMARY

Provided is a polypeptide for a photoresist, and a photoresist composition including the polypeptide. In addition, provided is an eco-friendly method of forming patterns, e.g., patterns in a semiconductor device, by using the photoresist composition in a patterning process.

Additional aspects will be set forth in part in the description which follows and, in part, will be apparent from the description, or may be learned by practice of the presented embodiments of the disclosure.

A polypeptide according to an aspect includes a region A and a region B, wherein the region A may have an alanine content of 20% or more and may include at least one first repeat unit having 4 to 10 consecutive amino acid residues, and the region B may have tyrosine in a content of 10% or more, and may have a content of 5% or more of at least one of serine, threonine, asparagine, or glutamine, and one or more second repeat units including 4 to 10 consecutive amino acid residues.

In region B, a content of tyrosine to a content of at least one of serine, threonine, asparagine, or glutamine in the second repeat unit may provide a ratio of 7:3 to 3:7.

In region B, a tyrosine and the at least one of serine, threonine, asparagine, or glutamine may be adjacent to each other and form a peptide bond.

In region B, an amino group of the tyrosine and a carboxyl group of the serine, threonine, asparagine, or glutamine may form a peptide bond.

The first repeat unit may be represented by the following Formula 1, and the second repeat unit may be represented by the following Formula 2:

Formula 1

Formula 2 wherein, in Formulae 1 and 2,
$X_{11}$ and $X_{12}$ are each independently Gly or Ala,
$X_{13}$ is Ser or Ala, and
n11 is an integer of 1 to 4; and
$X_{21}$ and $X_{23}$ are each independently Gly or Ala,
$X_{22}$ and $X_{24}$ are each independently Gly, Ala, or Val,
$X_{25}$ is Ser, Thr, Asn, or Gln,
n21 is an integer of 0 to 3, n22 is an integer of 1 to 4, and the sum of n21 and n22 is an integer of 1 to 4.

In Formulae 1 and 2, $X_{11}$ and $X_{12}$ may each be Gly, $X_{13}$ may be Ser, n11 may be 1 or 2; and $X_{21}$ and $X_{23}$ may each be Gly, $X_{22}$, $X_{24}$ may each independently be Ala or Val, $X_{25}$ is Ser, Thr, Asn, or Gln, and n21 may be an integer of 0 to 2, n22 may be 1, and the sum of n21 and n22 may be 1, 2, or 3.

In a polypeptide according to an embodiment, the first repeat unit may be Gly-Ala-Gly-Ala-Gly-Ser (SEQ ID NO:1) or Gly-Ala-Ala-Ser (SEQ ID NO:2), and the second repeat unit may be Gly-Ala-Ser-Tyr (SEQ ID NO:3), Gly-Ala-Gly-Ala-Ser-Tyr (SEQ ID NO:4), Gly-Ala-Gly-Val-Gly-Ala-Ser-Tyr (SEQ ID NO:5), or Gly-Ala-Gly-Ala-Gly-Ala-Ser-Tyr (SEQ ID NO:6).

In a polypeptide according to an embodiment, the region A may include 1 to 7 first repeat units, and the region B may include 1 to 20 second repeat units.

A ratio of the number of the first repeat unit to the number of the second repeat unit may be about 1:1 to about 1:x, where x is a real number greater than 1.

A polypeptide according to an embodiment may further include a region H including -Gly-Ala-Ala-Ser (SEQ ID NO:8).

The region H may be represented by Formula 3:

Formula 3 wherein, in Formula 3,
$X_{31}$ and $X_{32}$ are each independently Gly or Ala, $X_{33}$ is Ser or Ala, and n31 is 1 or 2.

The region H may be -Gly-Ala-Gly-Ala-Gly-Ser-Gly-Ala-Ala-Ser (SEQ ID NO:7).

A photoresist composition according to another aspect may include the polypeptide described above and water.

The photoresist composition may have a polypeptide concentration of about 0.1 percent weight per volume (w/v %) to about 20 w/v %.

A method of forming patterns according to still another aspect includes:
applying the photoresist composition with a polypeptide concentration of about 0.1 w/v % to about 20 w/v % onto a substrate;
heating the photoresist composition to form a photoresist film;
exposing at least a portion of the photoresist film to high-energy light; and developing the exposed photoresist film with a developer.

In the method, the heating may be performed at about 50° C. to about 95° C.

In the method, the high-energy light may have a wavelength of 200 nanometers (nm) or less.

In the method, the high-energy light may be sourced from an ArF excimer laser having a wavelength of 193 nm.

In the method, developer may consist of water.

In the method, the portion of the photoresist film exposed to the high-energy light may be water-soluble, and a portion of the photoresist film not exposed may be water-insoluble.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 2(a) is a side cross-sectional view of a photoresist film applied to a substrate;

FIG. 2(b) is a side cross-sectional view representation of exposing a masked photoresist film of FIG. 2(a) with light; and FIG. 2(c) is a side cross-sectional view of the developed (patterned) photoresist film of the light exposed photoresist film of FIG. 2(b).

DETAILED DESCRIPTION

Reference will now be made in detail to embodiments, embodiments of which are illustrated in the accompanying drawings, wherein like reference numerals refer to like elements throughout. In this regard, the present embodiments may have different forms and should not be construed as being limited to the descriptions set forth herein. However, the present invention is not limited by the present disclosure of the particular embodiments, and it should be understood that the present disclosure covers all the modifications, equivalents, and replacements within the idea and technical scope of the present disclosure. In describing the present disclosure, detailed descriptions of related known art will be omitted when it is determined that the detailed descriptions may obscure the gist of the present disclosure.

It will be understood that, although the terms "first," "second," "third," etc., may be used herein to describe various elements, components, regions, layers and/or sections, and the terms are only used to distinguish one element component, region, layer, and/or section, from another element, component, region, layer, or section. Thus, "a first element," "component," "region," "layer," or "section" discussed below could be termed a second element, component, region, layer, or section without departing from the teachings herein.

As used herein, when an element such as a layer, a film, a region, or a substrate is referred to as being "on" or "above" another element, it may be above, below, left, or right and directly on the other element or intervening elements may be present therebetween. In contrast, when an element, a layer, a film, or a region, is referred to as being "directly on" another element, there are no intervening elements present.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" indicates the presence of a characteristic, a number, a phase, a movement, an element, a component, or combinations of components described in the specification, and it should not be construed to exclude in advance the existence or possibility of existence of at least one of other characteristics, numbers, movements, elements, components, or combinations of components.

Wherever a range of values is recited, that range includes every value falling within the range, as if written out explicitly, and further includes the values bounding the range. Thus, a range of "from X to Y" includes every real number value falling between X and Y, and includes X and Y.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or ±5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, thicknesses of layers and regions are enlarged for a clear description. In addition, in the drawings, thicknesses of some layers and regions are exaggerated for convenience of description. Meanwhile, embodiments described herein are merely examples and various forms of modifications from these embodiments are possible.

Polypeptide

As used herein, the term "repeat unit" refers to four or more consecutive amino acid residues, i.e., four or more amino acid residues in a continuous, uninterrupted stretch within a polypeptide, and refers to a subsequence that is repeated within a larger sequence. In this case, it is not necessary that only sequences with exactly identical repeat units be repeated. Repeat units may include variable compositional elements, and due to the variable compositional elements, each repeat unit may vary randomly within the same region. The repeat unit (i.e., subsequence), may be repeated consecutively or non-consecutively. For example, the subsequences may be repeated with no intervening amino acids, or with one or more intervening amino acids between the subsequences, where each intervening amino acid may be the same or different.

As used herein, the term "region" refers to two or more consecutive amino acid residues in a continuous (i.e., a consecutive or an uninterrupted) stretch within a polypeptide, and a region includes at least one repeat unit.

A polypeptide according to example embodiments includes: a region A, wherein the region A may have an alanine content of 20% or more and may include at least one first repeat unit having 4 to 10 consecutive amino acid residues; and a region B, wherein the region B may have tyrosine in a content of 10% or more, and may have a content of 5% or more of at least one of serine, threonine, asparagine, or glutamine, and further includes one or more second repeat units including 4 to 10 consecutive amino acid residues.

In an embodiment, the region A and the region B may be consecutively arranged in the polypeptide. That is, the polypeptide may have no other sequence present between the region A and the region B, and the C-terminal of the region A and the N-terminal of the region B may form a peptide bond. In another embodiment, the polypeptide may consist of the region A and the region B.

The polypeptide includes 4 or more, 6 or more, 10 or less, or 8 or less amino acid residues within each of the first repeat unit and the second repeat unit.

The region A may include alanine (Ala). Specifically, since the region A has alanine content of 20% or more, and one or more first repeat units including 4 to 10 consecutive amino acid residues, an amount of alanine in the region A may be 20% or more, 25% or more, 30% or more, 35% or more, 40% or more, and 50% or less, or 45% or less. The first repeat unit may have an alanine content of 20% or more, 25% or more, 30% or more, 35% or more, 40% or more, and 50% or less, or 45% or less. Here, the alanine content in the region A is calculated as a percentage of a number of alanine residues with respect to a total number of amino acid residues of the region A. Likewise, the alanine content in the first repeat unit is calculated as a percentage of a number of alanine residues with respect to a total number of amino acid residues of the first repeat unit. The region A may include, or may consist of a sequence that is capable of forming a β-strand. Although not limited to a particular theory, since the region A includes alanine, it may be relatively hydrophobic and may form a crystalline region that is facilitated by a β-sheet stacking.

The region B may include tyrosine (Tyr). Specifically, because the region B has tyrosine content of 10% or more and one or more second repeat units including 4 to 10 consecutive amino acid residues, an amount of tyrosine in the region B may be 10% or more, 15% or more, 20% or more, 25% or more, 30% or more, and 40% or less, or 35% or less. The second repeat unit may have a tyrosine content of 10% or more, 15% or more, 20% or more, 25% or more, 30% or more, and 40% or less, or 35% or less. Here, the tyrosine content in the region B is calculated as a percentage of a number of tyrosine residues with respect to a total number of amino acid residues of the region B. Likewise, the tyrosine content in the second repeat unit is calculated as a percentage of a number of tyrosine residues with respect to a total number of amino acid residues of the second repeat unit. The region B may be a sequence having reactivity to high-energy light. Although not limited to a particular theory, because the region B includes tyrosine, it may react to light radiation having a wavelength of 200 nm or less, or specifically, 193 nm. Particularly, in the region B under a high-energy radiation, the bond between the phenyl ring of tyrosine and the main backbone chain may be broken to form a quinone methide, and the quinone methide may break the hydrogen bonds between β sheets of the region A. This type of photo-reactivity may result in a change of the solubility of the polypeptide in water. Accordingly, because of the presence of the region B, the solubility of the polypeptide in water is changed by high-energy light.

The region B may include at least one of serine, threonine, asparagine, and glutamine. Specifically, because the region B has one or more of serine, threonine, asparagine, or glutamine in a content of 5% or more, and one or more second repeat units including 4 to 10 consecutive amino acid residues, an amount of serine, threonine, asparagine, or glutamine in the region B may be 5% or more, 10% or more, 15% or more, 20% or more, 25% or more, 30% or more, and 40% or less, or 35% or less. The second repeat unit may have serine, threonine, asparagine, or glutamine in a content of 5% or more, 10% or more, 15% or more, 20% or more, 25% or more, 30% or more, and 40% or less, or 35% or less. Here, the amount of serine, threonine, asparagine, or glutamine in the region B is calculated as a percentage of a number of serine, threonine, asparagine, or glutamine residues with respect to a total number of amino acid residues of the region B. Likewise, the amount of serine, threonine, asparagine, or glutamine in the second repeat unit is calculated as a percentage of a number of serine, threonine, asparagine, or glutamine residues with respect to a total number of amino acid residues of the second repeat unit. Polar non-ionic amino acids such as serine, threonine, asparagine, or glutamine included in the region B may improve reactivity to light radiation having a wavelength of 200 nm or less, or specifically, 193 nm.

A content of tyrosine to a content of at least one of serine, threonine, asparagine, or glutamine in the second repeat unit may be present at a ratio of 7:3 to 3:7. A content of tyrosine to a content of at least one of serine, threonine, asparagine, or glutamine in the second repeat unit may be present at a ratio of 6:4 to 4:6. A content of tyrosine to a content of one or more of serine, threonine, asparagine, or glutamine in the second repeat unit may be the same, i.e., a ratio of about 1:1 or about 1.2:1 to 1:1.2

The relative positions of tyrosine and at least one of serine, threonine, asparagine, or glutamine are not limited in any way in the region B. For example, when the tyrosine and the at least one of serine, threonine, asparagine, or glutamine are adjacent to each other and form a peptide bond, the reactivity to light radiation having a wavelength of 200 nm or less, or specifically, 193 nm may be further improved. More specifically, an amino group of the tyrosine and a carboxyl group of an adjacent serine, threonine, asparagine, or glutamine may form a peptide bond.

In an embodiment, the first repeat unit may be represented by the following Formula 1:

$$X_{11}\text{-}(Ala\text{-}X_{12})_{n11}\text{---}X_{13},\qquad\text{Formula 1}$$

wherein, in Formula 1, $X_{11}$ and $X_{12}$ are each independently Gly or Ala, $X_{13}$ is Ser or Ala, and n11 is an integer of 1 to 4.

In an embodiment of Formula 1, $X_{11}$ and $X_{12}$ may each be Gly, $X_{13}$ may be Ser, and n11 may be 1 or 2.

In an embodiment of Formula 1, the first repeat unit may be Gly-Ala-Gly-Ala-Gly-Ser (SEQ ID NO:1) or Gly-Ala-Ala-Ser (SEQ ID NO:2).

In an embodiment, the second repeat unit may be represented by the following Formula 2:

$$X_{21}\text{---}(X_{22}\text{---}X_{23})_{n21}\text{---}(X_{24}\text{---}X_{25})_{n22}\text{-Tyr},\qquad\text{Formula 2}$$

wherein, in Formula 2, $X_{21}$ and $X_{23}$ are each independently Gly or Ala, $X_{22}$ and $X_{24}$ are each independently Gly, Ala, or Val, $X_{25}$ is Ser, Thr, Asn, or Gln, n21 is an integer of 0 to 3, n22 is an integer of 1 to 4, and the sum of n21 and n22 is an integer of 1 to 4.

In an embodiment of Formula 2, $X_{21}$ and $X_{23}$ may each independently be Gly, $X_{22}$ and $X_{24}$ may each independently be Ala or Val, $X_{25}$ may be Ser, Thr, Asn or Gln, n21 may be an integer of 0 to 2, n22 may be 1, and the sum of n21 and n22 may be 1, 2, or 3.

In Formula 2, $X_{21}$ and $X_{23}$ may each independently be Gly, $X_{22}$ and $X_{24}$ may each independently be Ala or Val, $X_{25}$ may be Ser, n21 may be an integer of 0 to 2, n22 may be 1, and the sum of n21 and n22 may be 1, 2, or 3.

The second repeat unit may be Gly-Ala-Ser-Tyr (SEQ ID NO:3), Gly-Ala-Gly-Ala-Ser-Tyr (SEQ ID NO:4), Gly-Ala-Gly-Val-Gly-Ala-Ser-Tyr (SEQ ID NO:5), or Gly-Ala-Gly-Ala-Gly-Ala-Ser-Tyr (SEQ ID NO:6).

The polypeptide may include 1 to 20 repeat units in each region A or regain B. Specifically, the region A may include 1 to 7 first repeat units, and the region B may include 1 to 20 second repeat units. More specifically, the region A may include 1 or more, 2 or more, 3 or more, and 7 or less, 6 or less, or 4 or less, first repeat units. The region B may include 1 or more, 2 or more, 4 or more, 6 or more, and 20 or less, 16 or less, 12 or less, or 8 or less, second repeat units.

In an embodiment, a ratio of the number of the first repeat unit to the number of the second repeat unit may be about 1:1 to about 1:x, where x may be a real number greater than 1. Specifically, x may be a real number of 10 or less. More specifically, x may be a real number of 10 or less, 9 or less, 8 or less, 7 or less, or 6 or less. In an embodiment, a number ratio of the number of the first repeat unit to the number of the second repeat unit may be about 1:1 to about 1:4, about 1:1 to about 1:3, or about 1:2 to about 1:4. In particular, a ratio of the number of the first repeat unit to the number of the second repeat unit may be about 1:4 or about 1:3. When the ratio of the number of the first repeat unit to the number of the second repeat unit satisfies the range described above, a photoresist composition having both improved photosensitivity and pattern quality may be provided.

In an embodiment, the polypeptide may further include a region H including -Gly-Ala-Ala-Ser (SEQ ID NO:8). Specifically, the region A may be disposed between the region H and the region B. In a polypeptide, the region H, the region A, and the region B are consecutively arranged. That is, the polypeptide may have no other amino acid or sequence present between the region H and the region A, and no other amino acid or sequence between the region A and the region B. As a result, the C-terminal of the region H and the N-terminal of the region A may form a peptide bond. In another embodiment, the polypeptide may consist of the region H, the region A, the region B, and a region C.

The region H may include 4 to 10 consecutive amino acid residues.

The region H may be represented by Formula 3:

$X_{31}$-(Ala-$X_{32}$)$_{n31}$—$X_{33}$-Gly-Ala-Ala-Ser (SEQ ID NO: 15)      Formula 3 wherein, in Formula 3, $X_{31}$ and $X_{32}$ are each independently Gly or Ala, $X3_3$ is Ser or Ala, and n31 is 1 or 2.

The region H may be Gly-Ala-Gly-Ala-Gly-Ser-Gly-Ala-Ala-Ser (SEQ ID NO:7).

In an embodiment, the polypeptide may have a weight average molecular weight of 10,000 grams per mole (g/mole) or less, and specifically, the polypeptide may have a molecular weight of about 3,000 g/mole to about 10,000 g/mole. The polypeptide is clearly different from proteins that form fibers having a molecular weight of greater than 10,000 g/mole. When the polypeptide has a molecular weight of greater than 10,000 g/mole, the polypeptide may have reduced solubility in solvents, particularly water, and thus may not be suitable for preparing a photoresist composition. Accordingly, the polypeptide may not have a satisfactory viscosity for applying the photoresist composition to a substrate. When the molecular weight of the polypeptide satisfies the range described above, the polypeptide may have a viscosity and/or solubility suitable for use as a photoresist composition.

As used herein, "molecular weight" refers to a weight average molecular weight.

In an embodiment, the polypeptide may have a polydispersity index of 2 or less. Specifically, the polypeptide may have a polydispersity index of 1. The polypeptide is not obtained by being extracted from natural proteins, but obtained by using a microorganism-based protein production technology, and thus may have a low polydispersity index. As the polydispersity index of the polypeptide is relatively low, performances suitable for use as a photoresist composition, such as improved resolution, reduced line-edge-roughness (LER), and/or reduced line-width-roughness (LWR) may be provided.

In an embodiment, the polypeptide may have a crystallinity of 40% or more. Specifically, the polypeptide may have a crystallinity of 43% or more. When the crystallinity satisfies the range described above, reduced LER and/or reduced critical dimension (CD) may be provided. A method of determining a crystallinity is described later.

Photoresist Composition

A photoresist composition according to example embodiments may include the polypeptide described above and water.

In an embodiment, the photoresist composition may consist of the polypeptide and water. Unlike photoresist compositions of the related art that include organic solvents, matrix materials, and the like, the photoresist composition in accordance with an embodiment including a polypeptide and water may alone function as a photoresist composition. For example, a photoresist composition in accordance with an embodiment may not include organic resins known in the photoresist art or non-alcoholic organic solvents. The use of peptide and water, which are generally recognized by those of ordinary skill to be eco-friendly materials, as a photoresist composition may reduce the frequency of exposure to toxic substances in semiconductor manufacturing processes, may simplify the disposal of waste liquid generated after the semiconductor manufacturing processes, and therefore, significantly reduce the costs of production. In addition, as a photoresist composition described herein is not a chemically amplified photoresist, it does not cause image degradation due to acid diffusion, which is a technical shortcoming of a chemically amplified photoresist. Accordingly, a photoresist composition described herein may be used to form relatively high resolution or precise patterns, e.g., patterns in a semiconductor device.

The photoresist composition may have a polypeptide concentration of about 0.1 percent weight per volume (w/v %) to about 20 w/v %. Specifically, the photoresist composition may have a polypeptide concentration of about 0.5 w/v % to about 10 w/v %.

Method of Forming Patterns

Figure 1:
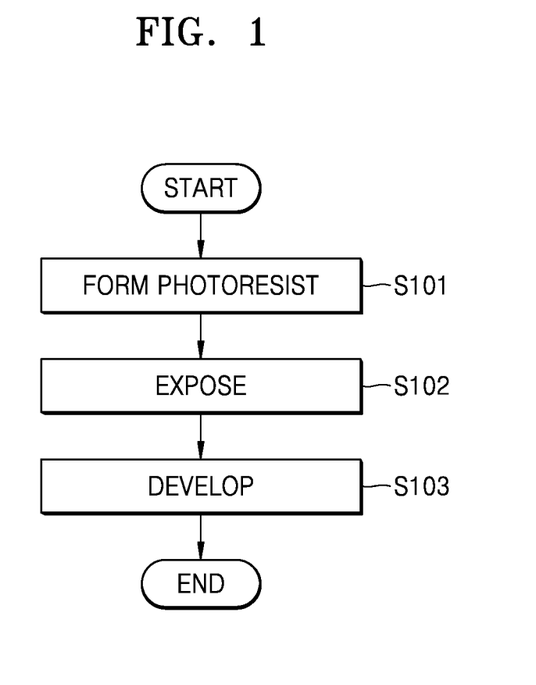
FIG. 1 is a flowchart showing a method of forming patterns, according to an embodiment of the present disclosure.
Figure 2:
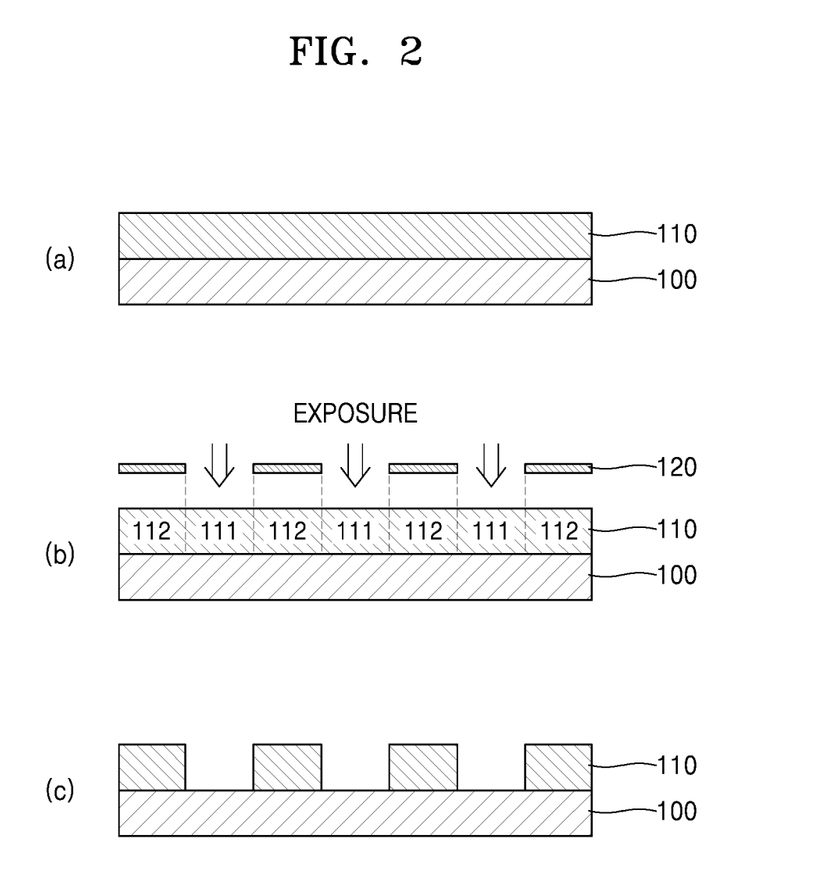
FIG. 2 is a side cross-sectional view showing a method of forming patterns, according to an embodiment of the present disclosure.

Hereinafter, a method of forming patterns according to one or more embodiments will be described in more detail with reference to FIGS. 1 and 2. FIG. 1 is a flowchart showing a method of forming patterns, according to an embodiment, and FIG. 2 is a side cross-sectional view showing a method of forming patterns according to an embodiment.

Referring to FIG. 1, a method of forming patterns includes: applying a photoresist composition according to an embodiment onto a substrate; heating the applied photoresist composition to form a photoresist film (S101); exposing at least a portion of the photoresist film to high-energy light (S102); and developing the exposed photoresist film with a developer (S103).

As depicted in FIGS. 2(a), 2(b), and 2(c), a substrate 100 is provided. Examples of the substrate 100 may include semiconductor substrates such as a silicon substrate or a germanium substrate, glass, quartz, ceramic, copper, or the like. In some embodiments, the substrate 100 may include a Group III-V compound such as GaP, GaAs, GaSb, or the like.

A photoresist composition according to an embodiment may be applied to the substrate 100 to a desired thickness using coating method to form a preliminary photoresist film (not shown), and the preliminary photoresist film may be heated to form a photoresist film 110, FIG. 1(a). Examples of the coating methods may include spin coating, dipping, roller coating, or other common coating methods known in the semiconductor art. Among the methods, particularly, spin coating may be used, and a photoresist film 110 having a desired thickness may be formed by regulating the viscosity, concentration, and/or spin speed of the photoresist composition. Specifically, the photoresist film 110 may have a thickness of about 10 nm to about 300 nm. More specifically, the photoresist film 110 may have a thickness of about 30 nm to about 200 nm.

When the photoresist composition is applied to the substrate 100, the polypeptide may be water-soluble due to the fact that the polypeptide has a molecular structure in the form of a random coil and thus, may have weak intermolecular attractions. As the polypeptide is water-soluble, the polypeptide needs to be made water-insoluble to provide a positive-tone development using water in a development process which will be described later. In this case, a method of heating a preliminary photoresist film to remove moisture may be used. Specifically, when the preliminary photoresist film is heated to remove moisture, the region A of the polypeptide may form a hydrogen bond and crystallize into a β-sheet structure, and accordingly, the polypeptide may become water-insoluble.

The heating may be performed at about 50° C. to about 95° C., or at about 80° C. to about 95° C. Heating at a relatively high temperature may increase the extent of crystallinity of the polypeptide, thereby providing reduced LER and/or reduced LWR.

The heating may be performed at a relative humidity of about 92% or greater.

The heating may be performed for about 1 hour to 20 hours, 2 hours or more, 4 hours or more, 6 hours or more, or 16 hours or more.

Before applying the photoresist composition to the substrate 100, an etching target film (not shown) may be further formed on the substrate 100. The etching target film may refer to a layer in which images are transcribed from photoresist patterns and converted into predetermined patterns. In an embodiment, the etching target film may include, for example, insulating materials such as silicon oxide, silicon nitride, or silicon oxynitride. In some embodiments, the etching target film may include conductive materials such as metal, metal nitride, metal silicide, or a metal silicide nitride film. In some embodiments, the etching target film may include semiconductor materials such as polysilicon.

In an embodiment, an anti-reflection film and a photoresist film may be sequentially formed on the etching target film.

Thereafter, at least a portion of the photoresist film 110 may be exposed using high-energy light, see, FIG. 2(b). For example, at least a portion of the photoresist film 110 may be exposed to high-energy light by using a mask 120 known in the art. Accordingly, the photoresist film 110 may have an exposed portion 111 and an unexposed portion 112. As described above, the bond between the phenyl ring of tyrosine and the main backbone chain is broken due to the irradiation of high-energy light onto the exposed portion 111 of the photoresist film 110 to form quinone methide. The quinone methide breaks the hydrogen bond between the β-sheets of the region A to change the solubility of the polypeptide in water, and thus, the polypeptide in the exposed region of photoresist film 111 becomes more water-soluble. Accordingly, the exposed portion 111 may be water-soluble and the unexposed portion 112 may be water-insoluble. Accordingly, the unexposed portion 112 is not removed by the developer, thereby providing a positive-tone development.

The high-energy light may have a wavelength of about 200 nm or less. Specifically, a source of the high-energy light may be an ArF excimer laser having a wavelength of about 193 nm, or an ozone lamp having a wavelength of about 184.9 nm. More specifically, the high-energy light may be sourced from ArF excimer laser having a wavelength of about 193 nm.

In an embodiment, with the use of an ArF excimer laser the exposed portion 111 may be irradiated for about 2 minutes to 10 minutes. In this case, an amount of irradiation per minute may be about 4 millijoules per square centimeter ($mJ/cm^2$) to about 60 $mJ/cm^2$, or about 10 $mJ/cm^2$ to about 20 $mJ/cm^2$.

Next, the exposed photoresist film 110 may be developed using a developer, see, FIG. 2(c). As the exposed portion 111 is water-soluble, the exposed portion 111 may be washed off by the developer, when, for example, water is used as a developer. As the unexposed portion 112 remains water-insoluble, it remains, i.e., without being washed off by the developer.

Examples of the developing method may include methods such as spin coating, dipping, or puddle coating, and a developing time effective to remove the exposed portion 111 is about 5 seconds to about 2 minutes, or about 1 minute.

In an embodiment, the developer may consist of water. When a developer consisting of water is used, the crystallized photoresist film 110 may be less affected by the developer. Accordingly, it may be easier to control the photoresist film 110 to a desired thickness than when using a developer including other organic solvents other than water, for example, methanol. In addition, since water is used as the developer and no additional additives are required, although time of exposure and productivity are maintained in a similar level as conventional methods in the overall process, water may simultaneously perform the functions of development and washing to provide a simplified process with significantly reduced costs and/or time. In particular, a method of making a pattern may reduce exposure to potentially toxic substances and/or reduce the need for organic solvents in the semiconductor patterning process.

The method of forming patterns according to an embodiment of the present disclosure may further include baking, etching, stripping, and the like, which are performed in a general photolithography process.

EXAMPLES

Synthesis Example 1: Synthesis of Polypeptide $HA_1B_4$

The following method was used to synthesize a polypeptide having a sequence of $HA_1B_4$ shown in Table 1.

TABLE 1

| No. of Synthesis Example | Name of polypeptide | Sequence |
|---|---|---|
| Synthesis Example 1 | $HA_1B_4$ | [N-terminal]-GAGAGSGAAS-GAGAGS-GAGAGY-GAGVGAGY-GAGY-GAGAGAGY-[C-terminal] (SEQ ID NO: 9) |
| Synthesis Example 2 | 14-A | [N-terminal]-GAGAGSGAAS-GAGAGS-GAGAAY-GAGVGAAY-GAAY-GAGAGAAY-[C-terminal] (SEQ ID NO: 10) |
| Synthesis Example 3 | 14-P | [N-terminal]-GAGAGSGAAS-GAGAGS-GAGAPY-GAGVGAPY-GAPY-GAGAGAPY-[C-terminal] (SEQ ID NO: 11) |
| Synthesis Example 4 | 14-S | [N-terminal]-GAGAGSGAAS-GAGAGS-GAGASY-GAGVGASY-GASY-GAGAGASY-[C-terminal] (SEQ ID NO: 12) |
| Synthesis Example 5 | 14-D | [N-terminal]-GAGAGSGAAS-GAGAGS-GAGADY-GAGVGADY-GADY-GAGAGADY-[C-terminal] (SEQ ID NO: 13) |
| Synthesis Example 6 | 14-K | [N-terminal]-GAGAGSGAAS-GAGAGS-GAGAKY-GAGVGAKY-GAKY-GAGAGAKY-[C-terminal] (SEQ ID NO: 14) |

In Table 1, G is Gly, A is Ala, S is Ser, V is Val, Y is Tyr, P is proline, D is aspartic acid, and K is lysine.

NcoI and XhoI restriction enzyme cleavage sites were set to be present at both ends of a nucleotide sequence that can produce $HA_1B_4$ polypeptide of Table 1, and the nucleotide was loaded into pUC57 vector to synthesize pUC57-$HA_1B_4$ vector. The synthesized pUC57-$HA_1B_4$ vector was treated with ThermoFisher Fermentas™ NcoI and XhoI restriction enzymes, electrophoresed on Bio-Rad Certified Molecular Biology agarose gel, and the gel was cut out and eluted with GeneAll Hybrid-Q™ to obtain $HA_1B_4$ synthetic gene DNA. pET30a vector DNA was obtained in the same manner as described above, mixed with the previously obtained $HA_1B_4$ synthetic gene DNA, and treated with Takara T4 DNA ligase at 16° C. for 2 hours. Thereafter, the obtained gene DNA was mixed with HITTM-DH5a competent cells, and the mixture was subjected to heat shock at 42° C. for 30 seconds to introduce DNA into the cells. The cells were streaked on Luria-Bertani (LB) solid medium containing kanamycin to obtain a colony into which a vector cloned with the synthetic gene in pET30a was introduced. The obtained colony was inoculated into 3 mL of LB liquid medium containing kanamycin and then shake-cultured at 37° C. and 250 rpm overnight. The colony was subjected to miniprep with GeneAll Hybrid-Q™ to obtain a vector, and the obtained vector was treated with ThermoFisher Fermentas™ NcoI and XhoI restriction enzymes. The vector was electrophoresed on Bio-Rad Certified Molecular Biology Agarose gel containing AB materials SafeView™, and observed through Bio-Rad Gel-Doc XR+ system to confirm that the synthetic gene was cloned into pET30a. Using such method, pET30a-$HA_1B_4$ vector into which the synthetic gene DNA was introduced was prepared and confirmed.

The pET30a-$HA_1B_4$ vector was mixed with Invitrogen BL21(DE3) competent cells, and the mixture was subjected to heat shock at 42° C. for 30 seconds to introduce DNA into the cells. The cells were streaked on LB solid medium containing kanamycin to obtain a colony. The obtained colony was inoculated into 3 mL of LB liquid medium containing kanamycin and then shake-cultured at 37° C. and 250 rpm overnight. The resulting culture solution (100 μl) was inoculated into 10 mL of LB liquid medium containing kanamycin, and grown until an optical density at a wavelength of 600 nm ($OD_{600}$)=0.5 at 37° C. and 250 rpm. The cells were further cultured at 37° C. and 250 rpm for 2 hours after 30 μl of 100 mM IPTG was added, and subjected to centrifugation at 5,000 rpm for 10 minutes to collect the colony. The collected colony was resuspended in 700 μl of a pH 8.0 Tris-Cl solution, and the cells were disrupted for 2 minutes at an amplitude of 25% using Sonics VCX-130 Ultrasonicator and subjected to centrifugation at 15,000 rpm for 10 minutes to obtain a supernatant. The supernatant, 75 μl, and 25 μl of Bio-Rad 4× Laemmli Sample Buffer™ were mixed and treated at 95° C. for 5 minutes, and 15 μl of the mixture was loaded on Bio-Rad Any-kD™ gel, electrophoresed at 200 V for 30 minutes using a Bio-Rad Mini-PROTEAN device, and stained with Bio-Rad Coomassie Brilliant Blue R-250 Staining Solution to confirm the expression of the synthetic gene. Using such a method, a protein-producing colony was prepared, and the expression was confirmed.

The colony confirmed to have the desired polypeptide expression was inoculated in 50 mL of LB liquid medium containing kanamycin and then shaking-cultured at 37° C. and 250 rpm overnight. The resulting culture solution, 100 μl, was inoculated into 1 L of LB liquid medium containing kanamycin, grown until $OD_{600}$=0.5 at 37° C. and 250 rpm, and then further cultured at 37° C. and 250 rpm for 3 hours after 300 μl of 1 M IPTG was added. The obtained was subjected to centrifugation at 5,000 rpm for 10 minutes to collect the colony. The collected colony was resuspended in 10 mL of a pH 8.0 Tris-Cl solution, and the cells were disrupted for 5 minutes at an amplitude of 40% using Sonics VCX-750 Ultrasonicator and subjected to centrifugation at 15,000 rpm for 30 minutes to obtain a supernatant. The obtained supernatant was passed through 1 mL of Qiagen Ni-NTA agarose resin, passed through 15 mL of a pH 8.0 Tris-Cl solution containing 10 mM imidazole to wash the resin, and lastly the resin was eluted with 3 mL of a pH 8.0 Tris-Cl solution containing 100 mM imidazole to purify a desired polypeptide. 15 µl of the purified polypeptide and 5 µl of Biorad 4× Laemmli Sample Buffer™ were mixed, heated at 95° C. for 5 minutes, 5 µl the resulting mixture was loaded to Bio-Rad Any-kD™ gel, electrophoresed at 200 V for 30 minutes using a Bio-Rad Mini-PROTEAN device, and stained with Bio-Rad Coomassie Brilliant Blue R-250 Staining Solution to confirm the desired polypeptide.

Synthesis Examples 2 to 6: Synthesis of Polypeptide

Polypeptides were synthesized in the same manner as in Synthesis Example 1, except that site directed mutagenesis was used to clone instead of pET30a-$HA_1B_4$ vector to obtain a vector that can produce polypeptides of Synthesis Examples 2 to 6 described in Table 1.

Evaluation Example 1: Evaluation of Photoresist Characteristics Sample Preparation The purified protein solution obtained in the synthesis examples was concentrated to 3.5 w/v % using Merck Amicon® Stirred Cells™ and Ultracell 1 Kda membrane filter. Thermo-Fisher SnakeSkin™ dialysis tubing (3.5K MWCO 16 mm ID) was cut to 7 cm in length, soaked in 500 mL of tertiary distilled water for 15 minutes, and taken out, and the tubing was washed inside and outside three times using 50 mL of tertiary distilled water. Then, 5 mL of a sample was put into the washed tubing, which was closed at both sides with forceps, and the dialysis tubing containing the sample concentrated to 3.5 w/v % was put in 1 L of tertiary distilled water and subjected to dialysis at 20° C. for 4 hours by replacing the distilled water with 1 L of fresh tertiary distilled water every 1 hour to obtain a 3.5 w/v % polypeptide aqueous solution.

TABLE 2

| No. of Sample | Polypeptide |
| --- | --- |
| Ref. Sample 1 | $HA_1B_4$ |
| Ref. Sample 2 | 14-A |
| Ref. Sample 3 | 14-P |
| Ref. Sample 4 | 14-D |
| Ref. Sample 5 | 14-K |
| Sample 1 | 14-S |

Evaluation of Photoresist Characteristics

A 1.5 cm square silicon wafer was washed for 30 minutes using a Jelight UVO144AX-220 UV-ozone cleaner, 100 µl of Reference Samples 1 to 5 and Sample 1 were each applied on the silicon wafer, and spin-coated at 300 RPM for 5 seconds, at 3000 RPM for 40 seconds, and at 500 RPM for 5 seconds using MIDAS Spin Controller to a thickness of 50 nm. The spin-coated wafer was dried at 95° C. for 1 minute using a Daehan Scientific HP-LP hot plate, and then treated for 16 hours at 95° C. and 92% humidity using an ESPAC SH-661 thermo-hygrostat to remove moisture and to form a polypeptide film. The silicon wafer on which the polypeptide film was formed was stored in a desiccator until it was exposed to high energy light.

Evaluation of Line Width (LW) and Line Width Roughness (LWR)

A pattern mask was placed on the silicon wafer on which the polypeptide film was formed, and the sample was exposed using an ArF excimer laser with various exposure amounts of 8.48, 12.71, and 25.42 mJ/cm². Following exposure• The wafers are dipped in water for 1 minute to develop.

The pattern mask was prepared by performing a lithography on a fused silica using E-beam, and lifting-off, and has 500 nm line and space (L/S) patterns.

Line width (LW) is an average of values obtained from 10 sites in the longitudinal direction of the line of the pattern using an atomic-force microscopy equipment. The higher the value, a sample is evaluated to have the higher sensitivity.

Line width roughness (LWR) was obtained by measuring values from 10 sites in the longitudinal direction of the line of the pattern using an atomic-force microscopy equipment and calculating the standard deviation times 3 (3σ), which is line width roughness. The smaller the value, the smaller the roughness, and a pattern of uniform line width may be obtained.

LW and LWR values evaluated for Reference Samples 1 to 5 and Sample 1 were shown in Tables 3 and 4 below. Specifically, Table 3 shows LW and LWR values when an exposure amount is 12.71 mJ/cm².

TABLE 3

| | | | Exposure amount (12.71 mJ/cm²) | |
| --- | --- | --- | --- | --- |
| Example No. | Sample No. | Polypeptide | LW (nm) | LWR (nm) |
| Ref. Example 1-1 | Ref. Sample 1 | $HA_1B_4$ | 382 | 9 |
| Ref. Example 1-2 | Ref. Sample 2 | 14-A | 294.1 | 18 |
| Ref. Example 1-3 | Ref. Sample 3 | 14-P | 588.2 | 31 |
| Ref. Example 1-4 | Ref. Sample 4 | 14-D | 529.4 | Impossible to measure |
| Ref. Example 1-5 | Ref. Sample 5 | 14-K | 588.2 | 26 |
| Example 1-1 | Sample 1 | 14-S | 544.1 | 11 |

TABLE 4

| | | | Exposure amount 8.48 (mJ/cm²) | | Exposure amount 12.71 (mJ/cm²) | | Exposure amount 25.42 (mJ/cm²) | |
| --- | --- | --- | --- | --- | --- | --- | --- | --- |
| Example No. | Sample No. | Polypeptide | LW (nm) | LWR (nm) | LW (nm) | LWR (nm) | LW (nm) | LWR (nm) |
| Ref. Example 1-1 | Ref. Sample 1 | $HA_1B_4$ | 260 | 18 | 397 | 11 | 490 | 10 |
| Example 1-1 | Sample 1 | 14-S | 320 | 17 | 525 | 11 | — | — |

Referring to Table 3, Example 1-1, wherein serine was included in a region B, showed similar or decreased LWR and a significantly improved sensitivity, compared to the Reference Examples 1-1 to 1-5. Specifically, Example 1-1 had LW 1.42 times greater than that of Reference Example 1-1, but a LWR value was maintained at a similar level.

Referring to Table 4, Example 1-1 showed similar level of LWR and significantly increased LW compared to Reference Example 1-1 regardless of the exposure amount. In addition, the test results of Reference Example 1-1 when an exposure amount was 25.42 mJ/cm$^2$ and the test results of Example 1-1 when an exposure amount was 12.71 mJ/cm$^2$ showed similar levels of LWR and LW, which indicates Example 1-1 has an improved sensitivity with little change in LWR.

An embodiment of the present disclosure can provide a photoresist composition having an improved sensitivity, improved LWR, and/or critical dimension (CD). In addition, when patterns are formed by using the photoresist composition, manufacturing processes are simplified and disposal cost for generated by-products are also reduced, and thus, manufacturing costs may be reduced.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A polypeptide comprising a region A, a region B, and a region H;
wherein:
the region A has an alanine content of 20% or more, and includes at least one first repeat unit having 4 to 6 consecutive amino acid residues, wherein the first repeat unit is represented by Formula 1:

$$X_{11}\text{-}(Ala\text{-}X_{12})_{n11}\text{---}X_{13};\qquad\text{Formula 1}$$

wherein $X_{11}$ and $X_{12}$ are each independently Gly or Ala, $X_{13}$ is Ser, and
n11 is 1 or 2;
the region B has a tyrosine content of 10% or more, a content of 5% or more of at least one of serine, threonine, asparagine, or glutamine, and includes at least one second repeat unit including 4 to 8 consecutive amino acid residues, wherein the second repeat unit is represented by Formula 2:

$$X_{21}\text{---}(X_{22}\text{---}X_{23})_{n21}\text{---}(X_{24}\text{---}X_{25})_{n22}\text{-Tyr};\qquad\text{Formula 2}$$

wherein $X_{21}$ and $X_{23}$ are each Gly,
$X_{22}$ and $X_{24}$ are each independently Ala or Val,
$X_{25}$ is Ser, Thr, Asn, or Gln,
n21 is an integer of 0 to 2, and
n22 is 1; and
the region H comprises Gly-Ala-Ala-Ser (SEQ ID NO: 8);
wherein the polypeptide has a molecular weight of 10,000 g/mol or less.

2. The polypeptide of claim 1, wherein the first repeat unit is Gly-Ala-Gly-Ala-Gly-Ser (SEQ ID NO: 1) or Gly-Ala-Ala-Ser (SEQ ID NO: 2); and
the second repeat unit is Gly-Ala-Ser-Tyr (SEQ ID NO: 3), Gly-Ala-Gly-Ala-Ser-Tyr (SEQ ID NO: 4), Gly-Ala-Gly-Val-Gly-Ala-Ser-Tyr (SEQ ID NO: 5), or Gly-Ala-Gly-Ala-Gly-Ala-Ser-Tyr (SEQ ID NO: 6).

3. The polypeptide of claim 1, wherein the region A includes 1 to 4 of the first repeat units, and the region B includes 2 to 12 of the second repeat units.

4. The polypeptide of claim 1, wherein the ratio of the number of the first repeat unit to the number of the second repeat unit is about 1:1 to about 1:x, and wherein x is any real number greater than 1.

5. The polypeptide of claim 1, wherein the region H is represented by Formula 3:

$$X_{31}\text{-}(Ala\text{-}X_{32})_{n31}\text{---}X_{33}\text{-Gly-Ala-Ala-Ser (SEQ ID NO: 15)};\qquad\text{Formula 3}$$

wherein in Formula 3, $X_{31}$ and $X_{32}$ are each independently Gly or Ala; $X_{33}$ is Ser or Ala; and n31 is 1 or 2.

6. The polypeptide of claim 1, wherein the region H is Gly-Ala-Gly-Ala-Gly-Ser-Gly-Ala-Ala-Ser (SEQ ID NO: 7).

* * * * *